United States Patent [19]
Sangekar et al.

[11] Patent Number: 5,846,971
[45] Date of Patent: Dec. 8, 1998

[54] ORAL ANTIFUNGAL COMPOSITION

[75] Inventors: Surendra A. Sangekar, Union; Winston A. Vadino, Whitehouse Station, both of N.J.; Ping I. Lee, Radnor, Pa.

[73] Assignee: Schering Corporation, Kenilworth, N.J.

[21] Appl. No.: 879,928

[22] Filed: Jun. 20, 1997

Related U.S. Application Data

[60] Provisional application No. 60/

[51] Int. Cl.$^6$ ............ A61K 31/495; A61K 31/675; A61K 31/54; A61K 31/535
[52] U.S. Cl. ............ 514/252; 514/85; 514/227.8; 514/236.2; 514/951
[58] Field of Search ............ 514/252, 85, 227.8, 514/236.2, 951

[56] References Cited

U.S. PATENT DOCUMENTS

| | | | |
|---|---|---|---|
| 4,791,111 | 12/1988 | Heeres et al. | 514/252 |
| 4,853,223 | 8/1989 | Graf et al. | 424/405 |
| 4,906,478 | 3/1990 | Valentine et al. | 424/682 |
| 5,039,676 | 8/1991 | Saksena et al. | 514/254 |
| 5,272,137 | 12/1993 | Blase et al. | 514/54 |
| 5,411,745 | 5/1995 | Oshlack et al. | 424/456 |
| 5,506,248 | 4/1996 | Nikfar et al. | 514/374 |
| 5,580,578 | 12/1996 | Oshlack et al. | 424/468 |
| 5,661,151 | 8/1997 | Saksena et al. | 514/252 |

FOREIGN PATENT DOCUMENTS

| | | |
|---|---|---|
| 0539938A1 | 5/1993 | European Pat. Off. . |
| 0 636 366 A2 | 2/1995 | European Pat. Off. . |
| WO 89/04829 | 5/1989 | WIPO . |
| WO94/05263 | 3/1994 | WIPO . |
| WO 95/17407 | 6/1995 | WIPO . |

OTHER PUBLICATIONS

Surelease Formulation Data for Overcoat Formulation containing Opadry (YS-1-7006), Technical Data by Colorcon, Inc., subsidiary of Berwind Corporation, West Point, PA, (1985), 2 pages.

Peter G. Welling, Pharmacokinetics, Processes and Mathematics, American Chemical Society, Washington, DC, ACS Monograph 185, (1986), p. 57.

J.G. Nairn, Remington's Pharmaceutical Sciences, 18th Edition, (1990), Mack Publishing Co., Chapter 83, p. 1519.

A.A. Nomeir et al., Bioavailability of SCH56592, a new broad spectrum triazole antifungl agent, from various formulations; Abstract of paper presented at 36th ICAAC, New Orleans, Louisiana, (Sep. 15–18, 1996); 1 page.

Pluronic® and Tetronic® Surfactants, publication of BASF Corporation, Mount Olive, New Jersey (1989), 29 pages.

Pluronic®Block Copolymer NF Grade (Poloxamer NF Grades); Technical Bulletin of BASF Corporation, (1995), 2 pages.

W. C. Gunsel and J. L. Kanig, Chapter 11, Tablets, from The Theory and Practice of Industrial Pharmacy, 2nd Edition, Lea&Febiger, Philadelphia, (1976), pp. 321–344.

Van Hostetler and J.Q. Bellard, Chapter 13, Part I. Hard Tablets, from The Theory and Practice of Industrial Pharmacy, 2nd Edition, Lea&Febiger, Philadelphia, 1976, pp.389–404.

A. K. Saksena et al., Concise Asymmetric Routes to 2,2, 4–Trisubstituted Tetrahydrofurans via Chiral Titanium Imide Enolates: Key Intermediates Towards Synthesis of Highly Active Azole Antifungals SCH51048 and SCH56592, Tetrahedron Letters, vol. 37, No. 32, (1996), pp. 5657–5660.

D. Loebenberg et al., #46, Formulation studies with SCH56592, a new broad spectrum antifungal triazole, abstract of paper submitted at "Focus on Fungal Infections 6" in New Orleans, Louisiana, Mar. 6–8, 1996, 4 pages.

Sinkula in Annual Reports Medicinal Chemistry, vol. 10, Chapter 31, pp. 306–315 (1975).

*Primary Examiner*—Kevin E. Weddington
*Attorney, Agent, or Firm*—Joseph T. Majka

[57] ABSTRACT

A pharmaceutical composition comprising:

i) substantially inert beads; wherein said beads are coated with ii) an antifungal agent which is (−)-(2R-cis)-4-[4-[4-[4-[[-5-(2,4-difluorophenyl)tetrahydro-5-(1H-1,2,4-triazol-1-ylmethyl)furan-3-yl]methoxy]phenyl]-1-piperazinyl]phenyl]-2,4-dihydro-2-[(S)-1-ethyl-2(S)-hydroxypropyl]-3H-1,2,4-triazol-3-one;

iii) a binder to enables the antifungal compound to adhere to said beads.

The composition enables the antifungal compound, which has very low water solubility, to have enhanced bioavailability in mammals, such as humans.

19 Claims, No Drawings

ORAL ANTIFUNGAL COMPOSITION

This application claims benefit of USC Provisional appln. Ser. No. 60/020,666, filed Jun. 28, 1996.

BACKGROUND OF THE INVENTION

The present invention relates to compositions having enhanced or improved bioavailability for a novel triazole antifungal compound.

International Patent Publication Number WO 95/17407 published 29 Jun. 1995, teaches a novel class of tetrahydrofuran/triazole antifungal compounds. One particular compound, (2R-cis)-4-[4-[4-[4-[[-5-(2,4-difluorophenyl)tetrahydro-5-(1H-1,2,4-triazol-1-ylmethyl)furan-3-yl]methoxy]phenyl]-1-piperazinyl]phenyl]2-4-dihydro-2-[(S)-1-ethyl-2(S)-hydroxypropyl]-3H-1,2,4-Triazol-3-One ("the antifungal compound"), was found to have potent antifungal activity in suspensions against opportunistic fungi such as Aspergillis, Candida, Cryptococcus and other opportunistic fungi. However, solid compositions, such as powders or granules, were found to have reduced anti-fungal activity and/or bioavailability, presumably due to this compound's extremely low water solubility. It would be desirable to provide this antifungal compound in a pharmaceutical composition whose antifungal and/or bioavailabilty would be enhanced or improved.

SUMMARY OF THE INVENTION

The present invention is directed to a pharmaceutical composition comprising:

i) a plurality of beads; wherein said beads are coated with ii) an antifungal agent of the formula:

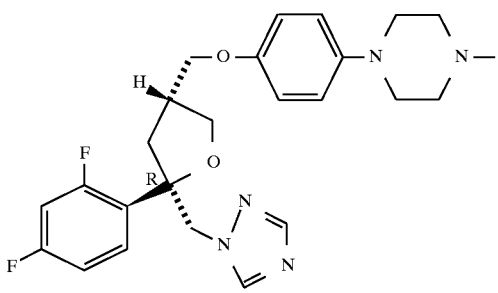

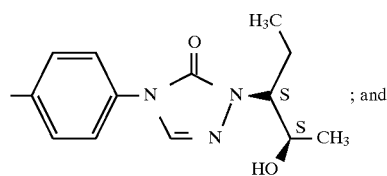

; and iii) a binder to enables the antifungal compound to adhere to said beads.

The pharmaceutical composition may also contain other excipients such as iv) surfactants, v) plasticizers, vi) defoaming agents and coloring agents. The pharmaceutical composition can also be formulated into any other suitable delivery system or dosage form, such as capsules, tablets, or beads for reconstitution.

It has also been surprisingly and unexpectedly found that the coating of beads with the antifungal compound using a suitable binder, can enhance or be equivalent to the bioavailability of the antifungal compound compared to suspensions. These results are truly surprising and unexpected, since known references, such as Peter G. Welling, Pharmacokinetics, Processes and Mathematics, American Chemical Society, Washington D.C., ACS Monograph 185, 1986, page 57, teaches that solutions and suspensions generally give rise to more satisfactory bioavailability than capsules or tablets. J. G. Nairn, Remington's Pharmaceutical Sciences, 18th Edition, 1990, Mack Publishing Co., Chapter 83, page 1519 also teaches that since drugs are absorbed in their dissolved state, frequently it is found that the absorption rate of oral dosage forms decreases in the following order: aqueous solution>aqueous suspension>capsule or tablet.

The present invention has the advantage of being able to provide the antifungal compound in a pharmaceutical composition that can conveniently be formulated into solid or "dry" delivery systems or dosage forms such as capsules, tablets or loose beads having effective antifungal activity and/or bioavailabilty.

DETAILED DESCRIPTION OF THE EMBODIMENTS

WO 95/17407 published 29 Jun. 1995 discloses antifungal compounds of the formula:

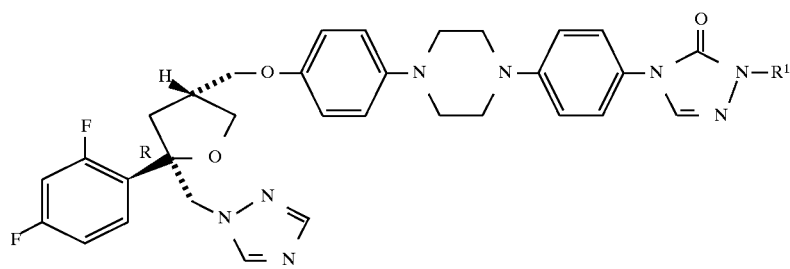

wherein $R^1$ is a straight or branch chain (C3 to C8) alkyl group substituted by one or two hydroxy moieties; esters and ethers thereof or a pharmaceutically acceptable salt thereof. An especially preferred compound of the above group taught in Examples 24 and 32 of WO 95/17407 is the antifungal compound, (−)-(2R-cis)-4-[4-[4-[4-[[-5-(2,4-difluorophenyl)-tetrahydro-5-(1H-1,2,4-triazol-1-ylmethyl)- furan-3-yl]methoxy]phenyl]-1-piperazinyl]phenyl]-2,-4-dihydro-2-[(S)-1-ethyl-2(S)-hydroxypropyl]-3H-1,2,4-triazol-3-one ("the antifungal compound"); Formula: $C_{37}H_{42}F_2N_8O_4$; Molecular weight: 700.8; m.p. 164°–165° C., $[a]_D^{25}$ –29° C.±3° (c=1.0, CHCl$_3$), whose structure is depicted below:

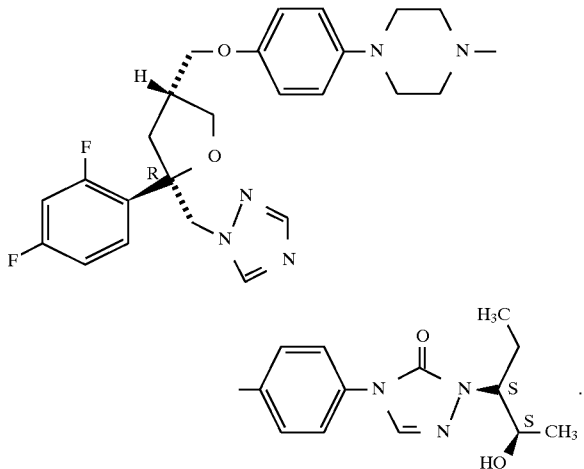

Micron-sized particles of the antifungal compound can be obtained either by the final step during the manufacture of the antifungal compound or by the use of conventional micronizing techniques after the conventional crystallization procedure(s).

Where micronizing techniques are employed, the antifungal compound may be micronized to the desired particle size range by conventional techniques, for example, using a ball mill, ultrasonic means, or preferably using fluid energy attrition mills such as the trost fluid energy mill from Plastomer Products, Newton, Pa. 18940. When using a fluid energy attrition mill, the desired particle size can be obtained by varying the feed rate of the antifungal into the mill.

About 99% of the of the micronized antifungal particle are less than or equal to 100 microns in length, of which 95% are less than or equal to 90 microns. Preferably, about 99% of the micronized particles are less than or equal to 50 microns, of which 95% are less than or equal to 40 microns. More preferably, 99% of the micronized particles are less than or equal to 20 microns, of which 95% are less than or equal to 10 microns.

The antifungal compound is employed in the composition in amounts effective to control the organism or fungi of interest. Such amounts can range from about 2% to about 50% by weight of the composition, more preferably from 6% to about 40%, most preferably from about 5 to about 33% by weight. The amount of composition in the particular dosage form, e.g. capsule, tablet, etc., can range from about 10 to about 300 mg antifungal compound per dosage form, preferably from about 50 to about 200 mg.

Compositions of the present invention can be prepared by dissolving or suspending the antifungal compound in an a suitable solvent system containing a binder, and optionally with one or more ingredients such as a surfactant, plasticizer, defoaming agent and/or coloring agent and coating the solution or suspension on the inert beads.

The pharmaceutical composition of the present invention can be formulated into any suitable dosage form, such as capsules, tablets or loose beads for constitution. For example, the above composition can be compressed into tablet form using a suitable cushioning agent, such as microcrystalline cellulose, and optionally, a disintegrant, lubricant, glident, and the like.

The following terms are used to describe the present pharmaceutical compositions, ingredients which can be employed in its formulation and methods for assessing its bioactivity or bioavailability.

The beads or seeds are discrete particles, preferably spherical particles or spheres, which serve as the solid substrate upon which the antifungal compound is coated, and make up the major portion of the composition or dosage form. Beads can be made of sugars such as lactose, sucrose, mannitol and sorbitol; other beads can be derived from starches derived from wheat, corn rice and potato; and celluloses such as microcrystalline cellulose. A source of sugar beads (non-pareil seeds) is known as Nu-pareil PG, tradename of Crompton and Knowles Ingredient Technology Corporation, of Mahawah, N.J. A source of microcrystalline cellulose beads is known as Celphere, tradename of the FMC Corporation, Philadelphia, Pa. Beads of differing mesh sizes can be employed, such as 18/20 mesh, 25/30 mesh and 40/50 mesh. Such mesh sizes refer to particle or bead sizes whose diameters can ranges from about 1.0 millimeters (mm) to about 0.297 mm. Preferably the bead sizes or diameters are within a relative narrow range such as, for example, between about 1.0–0.84 mm (18/20 mesh), or between about 0.71–0.59 mm (25/30 mesh), or between about 0.42–0.297 mm (40/50 mesh). The beads should be "inert" meaning that the beads themselves have little or no antifungal effectiveness. The amount of beads in the composition can range from about 50 to about 90% by weight of the total composition, preferably from about 60 to about 80%, more preferably from about 65 to about 75% by weight.

Binders—refers to substances that bind or "glue" the antifungal compound and other ingredients onto the beads, enabling the beads to be coated. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose, hydroxypropylcellulose, hydroxypropylmethylcellulose, hydroxyethylcellulose and sodium carboxymethylcellulose; polyvinylpyrrolidone (Povidones); protein hydrolysates; methacrylic acid and salts thereof; and inorganic compounds such as magnesium aluminum silicate. A commercially available formulation useful as a binder is known as Opadry powders, tradename of the Coloron Corporation, West Point, Pa. Opadry powders may contain hydroxypropylmethylcellulose, along with a plasticizer such as polyethylene glycol and a surfactant such as polysorbate-80. The amount of binder in the composition can range from about 1 to about 10% by weight of the composition, preferably from about 2 to about 8% by weight, more preferably from about 3 to about 6%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Surfactant—refers to a compound that can reduce the interfacial tension between two immiscible phases and this is due to the molecule containing two localized regions, one being hydrophilic in nature and the other hydrophobic.

Non-ionic surfactant—refers to a surfactant which lacks a net ionic charge and do not dissociate to an appreciable extent in aqueous media. The properties of non-ionic surfactants are largely dependent upon the proportions of the hydrophilic and hydrophobic groups in the molecule. Hydrophilic groups include the oxyethylene group ($—OCH_2CH_2—$) and the hydroxy group. By varying the number of these groups in a hydrophobic molecule, such as a fatty acid, substances are obtained which range from strongly hydrophobic and water insoluble compounds, such as glyceryl monostearate, to strongly hydrophilic and water-soluble compounds, such as the macrogols. Between these two extremes types include those in which the proportions of the hydrophilic and hydrophobic groups are more evenly balanced, such as the macrogol esters and ethers and sorbitan derivatives. Suitable non-ionic surfactants may be found in Martindale, The Extra Pharmacopoeia, 28th Edition, 1982, The Pharmaceutical Press, London, Great Britain, pp. 370 to 379. Such non-ionic surfactants include block copolymers of ethylene oxide and propylene oxide, glycol and glyceryl esters of fatty acids and their derivatives, polyoxyethylene esters of fatty acids (macrogol esters), polyoxyethylene ethers of fatty acids and their derivatives (macrogol ethers), polyvinyl alcohols, and sorbitan esters. Preferably, the non-ionic surfactant is a block copolymer of ethylene oxide and propylene oxide.

Suitable block copolymers of ethylene oxide and propylene oxide generically called "Poloxamers" and include those represented by the following chemical structure:

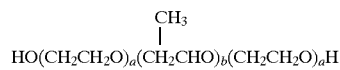

$$HO(CH_2CH_2O)_a(CH_2CHO)_b(CH_2CH_2O)_aH$$
with $CH_3$ branch on middle unit wherein a is an integer ranging from about 10 to about 110, preferably from about 12 to 101; more preferably from about 12 to 80; and b is an integer ranging from about 20 to about 60, more preferably from about 20 to about 56; also from about 20 to 27. Most preferably, a is 80 and b is 27, otherwise known as Pluronic®F68 surfactant, trademark of the BASF Corporation, Mount Olive, N.J., USA. Pluronic®F68 surfactant is also known as Poloxamer 188. This surfactant has an average molecular weight of 8400, is a solid at 20° C., has a viscosity (Brookfield) of 1000 cps at 77° C. Other suitable block copolymers of ethylene oxide and propylene oxide include Pluronic F87, also known as Poloxamer 237 wherein a is 64 and b is 37; and Pluronic F127, also known as Poloxamer 407 wherein a is 101 and b is 56.

Suitable glycol and glyceryl esters of fatty acids and their derivatives include glyceryl monooleate and similar water soluble derivatives;

Suitable polyoxyethylene esters of fatty acids (macrogol esters) include polyoxyethylene castor oil and hydrogenated castor oil derivatives;

Suitable polyoxyethylene ethers of fatty acids and their derivatives (macrogol ethers) include Cetomacrogel 1000, Lauromacrogols (a series of lauryl ethers of macrogols of differing chain lengths) e.g. Laureth 4, Laureth 9 and Lauromacrogol 400.

Suitable Sorbitan esters (esters of one or more of the hydroxyl groups in the sorbitans, with a fatty acid, such as stearic, palmitic, oleic or lauric acid) include, e.g. Polysorbate 20, Polysorbate 40, Polysorbate 60, Polysorbate 65, Polysorbate 80, Polysorbate 85, Sorbitan Monolaurate, Sorbitan Mono-oleate, Sorbitan Monopalmitate, Sorbitan Monostearate, Sorbitan Sesquioleate, Sorbitan Trioleate and Sorbitan Tristearate.

The amount of surfactant in the composition can range from about 0.5 to about 25% by weight of the total composition, more preferably from about 5 to about 15% by weight.

Anionic surfactant—refers to a surfactant which has a net negative ionic charge and dissociates to an appreciable extent in aqueous media. Optionally, the present composition may also contain an anionic surfactant, e.g. sodium lauryl sulfate, the amount of which can range from about 1 to about 10% by weight of the total composition, more preferably from about 3 to about 8% by weight.

Plasticizers—refers to substances which make the binder flexible. Suitable plasticizers include propylene glycol, glycerin, diethylphthalate, dibutyl sebacate, triethyl citrate, hydrogenated glycerides, polyethylene glycols, polyethylene oxides, triacetin and the like. The amount of plasticizer in the composition can be in the range of about 1–2 to about 5% by weight.

Defoaming agents, also known as antifoaming agents, are substances used to reduce foaming due to mechanical agitation or to gases, nitrogenous materials or other substances which may interfere during processing. Examples include metallic salts such as sodium chloride; C6 to C12 alcohols such as octanol; sulfonated oils; silicone ethers such as simethicone; organic phosphates and the like. The amount of defoaming agent in the composition can range from about 0.05 to 5%, preferably from about 0.1 to 2%.

Glidents—materials that prevent caking and improve the flow characteristics of granulations, so that flow is smooth and unifom. Suitable glidents include silicon dioxide and talc. The amount of glident in the composition can range from about 0.1% to about 5% by weight of the total composition, preferably from about 0.5 to about 2% by weight.

Lubricant—refers to a substance added to the dosage form to enable the tablet, granules, etc. after it has been compressed, to release from the mold or die by reducing friction or wear. Suitable lubricants include metallic stearates such as magnesium, calcium or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Dosage form—composition containing the antifungal compound formulated into a delivery system, i.e., tablet, capsule, oral gel, powder for constitution or suspension in association with inactive ingredients.

Capsule—refers to a special container or enclosure made of methyl cellulose, polyvinyl alcohols, or denatured gelatins or starch for holding or containing compositions comprising the active antifungal compound. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredient (antifungal compound) with suitable diluents. The tablet can be prepared by compression of mixtures or granulations obtained by wet granulation, dry granulation, compaction or compression of mixtures containing coated active beads.

Beads for constitution refers to the loose, coated beads which can be suspended in water, juices or sauces such as applesauce.

Bioavailability—refers to the rate and extent to which the active drug ingredient or therapic moiety is absorbed into the systemic circulation from an administered dosage form as compared to a standard or control.

$C_{max}$ values refers to the maximum concentration of the antifungal compound measured (i.e. "peak") in the plasma serum.

AUC (0–72 hr) values refer to the area under the plasma/serum concentration-time curve for the antifungal over a designated time.

Conventional methods for preparing tablets are known. Such methods include dry methods such as direct compression and compression of granulation produced by compaction, or wet methods or other special procedures.

The following examples describe compositions of the present invention containing the antifungal compound, but they are not to be interpreted as limiting the scope of the claims.

Example 1
Coated Beads in Capsules

| Ingredient | g/batch | % wt basis |
| --- | --- | --- |
| Antifungal compound, micronized | 135 | 20.3 |
| Opadry YS-1-7006 | 30 | 4.5 |
| Simethicone | 1.42 | 0.2 |
| Water purified, USP (evaporates) | 700 mL | — |
| Non-Pareil Seeds (25/30 mesh) | 500 | 75 |
| | 666.42 | 100% |

Example 2
Coated Beads in Capsules

| Ingredient | mg/batch | % wt basis |
| --- | --- | --- |
| Antifungal compound, micronized | 75 | 11.0 |
| Opadry YS-1-7006 | 30 | 4.4 |
| Pluronic F68 surfactant | 75 | 11.0 |
| Simethicone | 0.7 | 0.1 |
| Water purified, USP (evaporates) | 500 mL | — |
| Non-Pareil Seeds (25/30 mesh) | 500 | 73.5 |
| | 680.7 | 100% |

Preparation of Coated Beads in Capsules in Examples 1, 2 and 5

Dissolve the Opadry YS-1-7006, Pluronic F68 or sodium lauryl sulfate in water. Add simethicone while stirring. Add the antifungal compound while stirring slowly until a homogeneous suspension is formed. Screen the suspension through a 25 mesh hand screen. Spray the suspension onto the non-pareil seeds using a fluid bed coater. Dry the coated beads overnight and assay the coated beads to determine the amount of antifungal compound. Fill the coated beads into suitable size capsules to the requisite fill weight.

Preparation of Aqueous Suspension in Comparative Example 3

Prepare a suspension containing 59.8 mg Pluronic F68 in four mL of distilled water. Add 200 mg of antifungal compound to the above solution and mix to give a homogeneous suspension.

Preparation of Powder Mixture in Capsules in Comparative Example 4

| Ingredient | mg/capsule | % wt basis |
| --- | --- | --- |
| Antifungal compound, micronized | 100.0 | 28.6 |
| Sodium lauryl sulfate surfactant | 22.5 | 6.4 |
| Microcrystalline cellulose | 178.0 | 50.9 |
| Sodium starch glycolate | 45.0 | 12.8 |
| Magnesium stearate | 4.5 | 1.3 |
| | 350 | 100 |

Mix the antifungal compound, sodium lauryl sulfate (a surfactant), microcrystalline cellulose, and sodium starch glycolate in a blender for 10 minutes. Add magnesium stearate and mix for 5 minutes to form a homogeneous powder. Fill the powder into suitable size capsules to the requisite fill weight.

Testing for Bioavailability

Dogs are administered a 200 mg dose of the antifungal compound using two capsules or in suspension. Samples of serum are collected at selected times and analyzed by an HPLC/UV detection procedure using a high pressure liquid chromatograph equipped with an ultra-violet detector. In the table below, the $C_{max}$ and AUC (0–72 hr) values are indicators of the antifungal compound's bioavailability. The larger the AUC value, the greater the total amount of antifungal compound that accumulated in the plasma serum over the 72 hour period.

| Indicator of Bioavailibility: | Coated Beads in Capsules- Example 1 | Coated Beads in Capsules- Example 2 | Control Suspension- Comparative Example 3 | Powder Mixture in Capsules- Comparative Example 4 |
| --- | --- | --- | --- | --- |
| $C_{max}$ (ug/ml) | 1.43 | 1.37 | 1.21 | 0.95 |
| $AUC_{(0-72\ hr)}$ ug/hr/ml | 50.21 | 50.17 | 47.98 | 29.72 |

The results above show that capsules of Examples 1 and 2 exhibit enhanced bioavailability over that of the aqueous suspension of Comparative Example 3 and especially over the powdered mixture in capsules of Comparative Example 4.

Example 5
Coated Beads in Capsules

| Ingredient | g/batch | % wt basis |
| --- | --- | --- |
| Antifungal compound, micronized | 75.0 | 11.80 |
| Opadry YS-1-7006 | 30.0 | 4.72 |
| Sodium lauryl sulfate | 30.0 | 4.72 |
| Simethicone | 1.0 | 0.16 |

-continued

Example 5
Coated Beads in Capsules

| Ingredient | g/batch | % wt basis |
|---|---|---|
| Water purified, USP (evaporates) | 500 mL | — |
| Non-Pareil Seeds (25/30 mesh) | 500.0 | 78.60 |
|  | 636.0 | 100% |

What is claimed is:

1. A pharmaceutical composition comprising:
   i) a plurality of beads; wherein said beads are coated with
   ii) an antifungal agent of the formula:

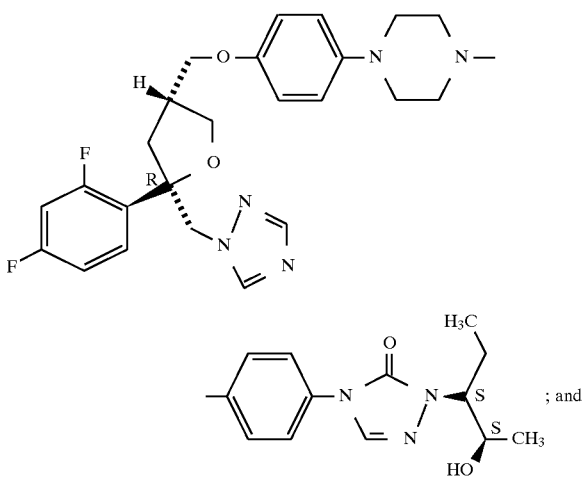

iii) a binder to enables the antifungal compound to adhere to said beads.

2. The composition of claim 1 wherein the beads are made of sugar, starch or microcrystalline cellulose.

3. The composition of claim 1 wherein the beads are made of sugar.

4. The composition of claim 1 wherein the beads have a mesh size ranging between about 18/20 to 45/50.

5. The composition of claim 1 wherein the amount of antifungal compound in the composition can range from about 5 to about 33% by weight.

6. The composition of claim 1 wherein the binder is hydroxypropylmethylcellulose.

7. The composition of claim 1 further comprising iv) a surfactant.

8. The composition of claim 7 wherein the surfactant is a non-ionic surfactant.

9. The composition of claim 7 wherein the surfactant is a block copolymer of ethylene oxide and propylene oxide.

10. The composition of claim 7 wherein the surfactant is an anionic surfactant.

11. The composition of claim 10 wherein the anionic surfactant is sodium lauryl sulfate.

12. The composition of claim 7 further comprising v) a plasticizer.

13. The composition of claim 12 wherein the plasticizer is polyethylene glycol.

14. The composition of claim 13 further comprising vi) a defoaming agent.

15. The composition of claim 14 wherein the defoaming agent is simethicone.

16. The composition of claim 1 in the dosage form of a capsule.

17. The composition of claim 16 wherein the amount of antifungal compound in the capsule is in the range of about 50 to 300 milligrams.

18. The composition of claim 16 wherein the amount of antifungal compound in the capsule is in the range of about 50 to 200 milligrams.

19. The pharmaceutical composition of claim 1 further comprising
    about 11–20% by weight of the antifungal compound;
    about 73–75% by weight beads;
    about 0.5–15% by weight of a surfactant;
    about 4.7–5% by weight of a binder which is hydroxypropylmethyl cellulose; and
    about 0.5–1.5% by weight of a defoaming agent.

* * * * *